United States Patent [19]

Wieringa

[11] Patent Number: 5,051,424
[45] Date of Patent: Sep. 24, 1991

[54] SUBSTITUTED AROMATIC COMPOUNDS HAVING AN ACTION ON THE CENTRAL NERVOUS SYSTEM

[75] Inventor: Johannes H. Wieringa, Heesch, Netherlands

[73] Assignee: Akzo N.V., Arnhem, Netherlands

[21] Appl. No.: 422,311

[22] Filed: Oct. 16, 1989

[51] Int. Cl.$^5$ ............... A61K 31/495; C07D 295/84; C07D 295/88
[52] U.S. Cl. ................... 514/255; 544/401; 544/398
[58] Field of Search ............... 544/401, 398; 514/255

[56] References Cited

U.S. PATENT DOCUMENTS 2,831,859  4/1958  Kindler et al. ............... 544/403
2,927,924  3/1960  Mills et al. ............... 544/393

FOREIGN PATENT DOCUMENTS 293532  12/1988  European Pat. Off. .

OTHER PUBLICATIONS

Southgate et al., Chem. Abst. 111—39092s (1989).

Primary Examiner—Cecilia Shen
Attorney, Agent, or Firm—William M. Blackstone; Donna Bobrowicz

[57] ABSTRACT

This invention relates to dopamine uptake-inhibiting compounds of the general formula I:

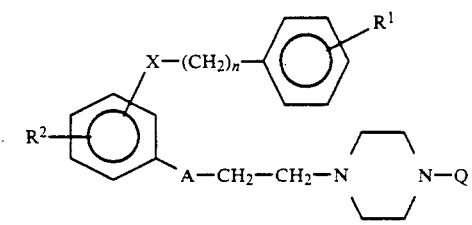

wherein
R$^1$ and R$^2$ independently are hydrogen, NO$_2$, OH, halogen, C$_1$-C$_4$ alkyl, C$_1$-C$_4$ alkoxy, unsubstituted amino or C$_1$-C$_4$ alkyl substituted amino;
X denotes O, S, CH$_2$, NH or NALK;
A represents C$_m$H hd 2m or C$_k$H$_{2k}$O;
l is 1 to 4;
m is 0 to 2;
n is 0 to 1;
Q represents hydrogen, phenyl or an ALK group optionally substituted by phenyl, wherein
ALK is a C$_1$-C$_6$ aliphatic hydrocarbon;
and the acid addition salts thereof.

5 Claims, No Drawings

SUBSTITUTED AROMATIC COMPOUNDS HAVING AN ACTION ON THE CENTRAL NERVOUS SYSTEM

The invention relates to novel di- and tri-substituted aromatic compounds of the general formula I:

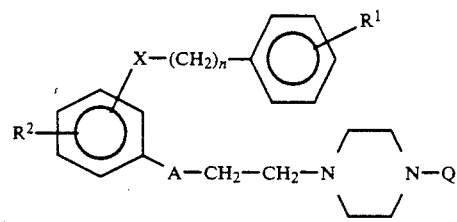

wherein
- $R^1$ and $R^2$ independently are hydrogen, $NO_2$, OH, halogen, $C_1$–$C_4$ alkyl, $C_1$–$C_4$ alkoxy, unsubstituted amino or $C_1$–$C_4$ alkyl substituted amino;
- X denotes O, S, $CH_2$, NH or NALK;
- A represents $C_mH_{2m}$ or $C_kH_{2k}O$;
- k is 1 to 4;
- m is 0 to 2;
- n is 0 or 1;
- Q represents hydrogen, phenyl or an ALK group optionally substituted by phenyl wherein
- ALK is a $C_1$–$C_6$ aliphatic hydrocarbon;

and the acid addition salts thereof.

The compounds according to the invention have an interesting anti-depressant action without a sedative side effect. The compounds are strong uptake inhibitors for monoamines, in particular for dopamine, and have no affinity with the histamine receptor. Consequently, in addition to use with patients suffering from depression, they can also be used in combating Parkinson's disease, in anxiety disorders, including agoraphobia, for the improvement of cognitive functions in patients suffering from dementia and as an appetite inhibitor.

Compounds of the general formula II:

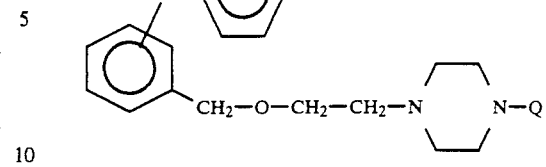

wherein $R^1$ and Q have the meaning given above and the acid addition salts thereof are the preferred group of compounds.

In particular, the compounds of the general formulae III and IV are highly potent:

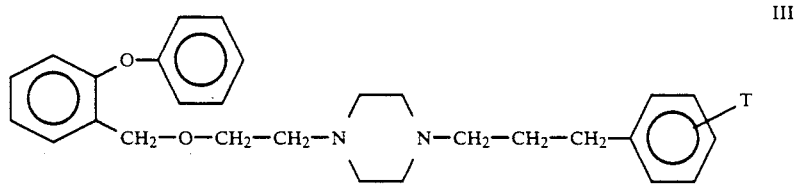

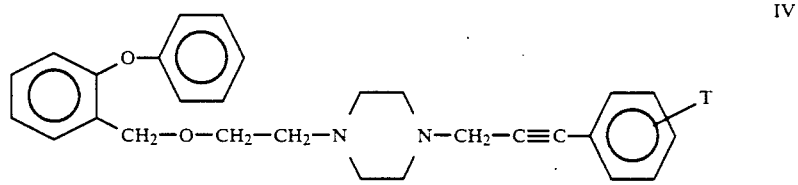

wherein T is hydrogen, $C_1$–$C_4$ alkyl or an amino group, as are also the acid addition salts thereof.

In the definition of compounds of the general formula I $C_1$–$C_4$ alkyl denotes saturated alkyl substituents having 1 to 4 carbon atoms, such as methyl, ethyl, propyl, isopropyl, butyl, isobutyl, sec-butyl and tert-butyl.

$C_1$–$C_4$ alkoxy denotes alkoxy substituents having 1 to 4 carbon atoms, in which the alkyl group has the above meaning.

A $C_1$–$C_6$ aliphatic hydrocarbon denotes branched and straight-chain, saturated and unsaturated hydrocarbons having 1 to 6 carbon atoms. Examples are ethyl, allyl, isopropenyl, propyl, ethynyl, butynyl, amyl, hexyl, allenyl and the like.

Phenyl denotes an unsubstituted phenyl group or a phenyl group substituted by OH, halogen, $NO_2$, unsubstituted amino or $C_1$–$C_4$ alkyl substituted amino, $C_1$–$C_4$ alkyl or $C_1$–$C_4$ alkoxy.

Acid addition salts of the compounds of the general formula I denote the salts of the compounds which are derived from pharmaceutically acceptable inorganic and organic acids. Customary acids are hydrochloric acid, sulphuric acid, phosphoric acid, acetic acid, propionic acid, fumaric acid, malonic acid, maleic acid, tartaric acid, citric acid, ascorbic acid, salicylic acid, benzoic acid and the like.

The compounds according to the invention can be prepared in a manner customary for analogous compounds.

In accordance with a general method of preparation, the piperazine group can be coupled directly to a compound of the general formula V:

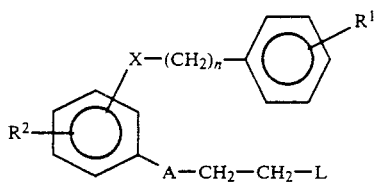

V wherein $R^1$, $R^2$, X, A and n have the meaning given above and L is leaving group, such as mesyl, tosyl, halogen and the like (Cl and Br are very suitable as the group L), by subjecting a compound V to a condensation reaction under slightly basic conditions and if necessary with heating in a suitable solvent, with a piperazine compound VI

VI wherein Q has the meaning given above.

Another suitable method for the preparation of compounds of formula I is the reduction of an amide of the general formula VII:

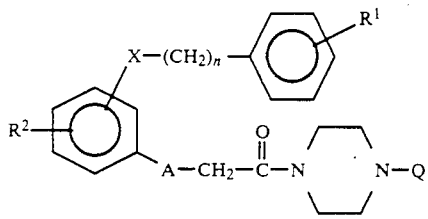

VII wherein $R^1$, $R^2$, Q, X, A and n have the meaning given above.

The reduction is preferably carried out with a metal hydride, for example LiAlH$_4$, in a suitable solvent, such as ether, tetrahydrofuran, benzene and the like.

The reaction is usually carried out at room temperature, but if necessary the solvent can be heated to the reflux temperature in the case of a reaction which is too slow, or can be cooled to about $-20°$ C. in the case of a reaction which is too vigorous.

A comparable method is the reduction of a diamide of the general formula VIII:

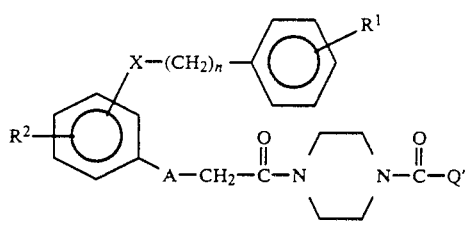

VIII wherein $R^1$, $R^2$, X, A and n have the meaning given above and Q' is ALK, optionally substituted by phenyl, with the proviso that the aliphatic hydrocarbon is one —CH$_2$— group shorter than the aliphatic hydrocarbon as defined for Q.

The reduction is carried out in the same way as described above for the amide of formula VII.

Compounds of general formula I wherein A is $C_kH_{2k}O$ can also be prepared by condensation reaction of the compounds IX and X:

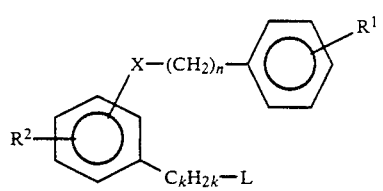

IX

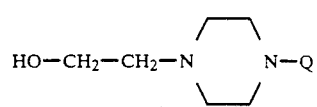

X wherein $R^1$, $R^2$, X, Q, k and n have the meaning given for general formula I and L has the meaning given for general formula V.

Compounds IX and X are coupled with the aid of a strong base, for example potassium tert-butylate or sodium hydride, in an inert solvent, such as ether, tetrahydrofuran, dimethoxy ethane and the like, usually with some warming, to give compounds of general formula I ($A=C_kH_{2k}O$).

It is also possible to convert a compound according to the invention into another compound according to the invention. An example is the conversion of a compound with Q is alkynyl to a compound with Q is alkenyl, which can be carried out by reaction with hydrogen in the presence of a suitable catalyst, for example a Lindlar catalyst. In a corresponding manner, the alkenyl group can be converted to an alkyl group. Similarly a benzyl group can be split off to hydrogen, by means of a reductive cleavage.

It is, of course, also possible to convert one substituent at one of the aromatic rings of a compound of formula I to another substituent within the definition of $R^1$ and $R^2$, for example, to convert an OH group to an alkoxy group, or a nitro group to an amino group.

Compounds of formula I wherein Q is hydrogen can preferably be prepared by hydrolysis of a formyl compound of the general formula XI:

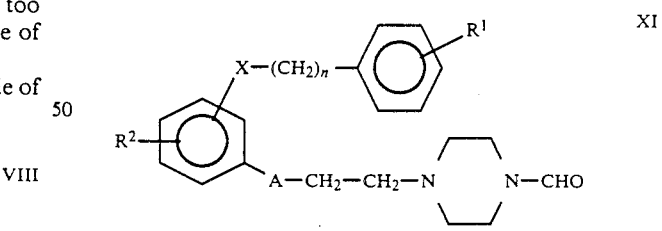

XI

Compound XI can be obtained, for example, by a condensation reaction of a compound of general formula V with N-formyl piperazine. Treatment of compound XI with a base, for example with aqueous solutions of sodium hydroxide solution or potassium hydroxide solution, sodium carbonate or sodium bicarbonate, yields the compound of general formula I wherein Q is H.

The compounds obtained by one of the hereinbefore described methods may be converted into their pharmaceutically acceptable salts by methods known in the art.

In the cases where compounds of the general formula I are chiral, the enantiomers also fall within the scope of the invention. The individual enantiomers can be obtained in the conventional manner by resolution of the racemate or by means of stereoselective synthesis.

The compounds according to the invention can be processed, by mixing with a pharmaceutically acceptable carrier or diluent, to pharmaceutical preparations for enteral or parenteral administration. A possible form of administration is, for example a tablet, pill, powder, capsule, emulsion, paste, spray or suppository. For outpatients the oral administration form will usually be preferred; for hospitalized patients administration by means of injections will also be frequently used.

The daily dosage is preferably 0.01–10 mg per kg bodyweight. For administration to humans, a dosage of 10 to 500 mg per day is preferred.

The following examples illustrate the invention.

EXAMPLE 1

1-[3-(3-methylphenyl)propyl]-4-[2-[2-phenoxyphenyl)-methoxy]ethyl]piperazine dihydrochloride A solution of 7.1 g (15.0 mmol) of 1-[1-oxo-2-[(2-phenoxyphenyl)methoxy]ethyl]-4-[3-(3-methylphenyl)-1oxopropyl]piperazine in a mixture of 120 ml of dry ether and 10 ml of dry tetrahydrofuran was added dropwise under nitrogen and with stirring to a suspension of 3.43 g (90.2 mmol) of lithium aluminium hydride in 250 ml of dry ether. The reaction mixture was stirred for 20 hours under nitrogen at room temperature and cooled to 5° C., after which 13.7 ml of water were carefully added dropwise. The precipitate was filtered off and the filtrate evaporated. The crude product was dissolved in 30 ml of ethanol to which 7 ml of 5 N HCl in ethanol was added. The precipitate was filtered off and recrystallized twice from 50 ml of ethanol. Yield 5.1 g (65%), m.p. 199° C.

EXAMPLE 2

The following compounds were prepared in a manner analogous to that described in Example 1:

1-[3-(3-methylphenyl)propyl]-4-[2-[(2-(phenylthio)-phenylmethoxy]ethyl]piperazine dihydrochloride, m.p. 226° C.

1-[2-[(2-phenylmethylphenyl)methoxy]ethyl]-4-(3-phenylpropyl)piperazine dihydrochloride, m.p. 209° C.

1-[2-[(4-phenoxyphenyl)methoxy]ethyl]-4-(3-phenylpropyl)piperazine dihydrochloride, m.p. 210° C.

1-[2-[(2-phenoxyphenyl)methoxy]ethyl]-4-(2-phenylethyl)piperazine dihydrochloride, m.p. 221° C.

EXAMPLE 3

1-[3-(2-chlorophenyl)propyl]-4-[2-[(2-phenoxyphenyl)-methoxy]ethyl]piperazine dihydrochloride A solution of 4.1 g (8.5 mmol) of 1-[3-(2-chlorophenyl)propyl]-4-[1-oxo-2-[(2-phenoxyphenyl)methoxy]ethyl]piperazine in 95 ml of dry ether was added dropwise, under nitrogen and with stirring, to a suspension of 1.26 g (33.1 mmol) of lithium aluminium hydride in 63 ml of dry ether. The reaction mixture was stirred at room temperature for 2 hours and cooled to 5° C., after which 5 ml of water were added dropwise. The precipitate was filtered off and the filtrate evaporated. The crude product was dissolved in 15 ml of ethanol, to which 4 ml of 5 N HCl in ethanol was added. The precipitate was filtered off and recrystallized from 20 ml of ethanol. Yield 2.8 g (61%), m.p. 200° C.

EXAMPLE 4

The following compounds were prepared in a manner analogous to that described in Example 3:

1-[3-(4-methylphenyl)propyl]-4-[2-[(2-phenoxyphenyl)-methoxy]ethyl]piperazine dihydrochloride, m.p. 225° C.

1-[3-(3-chlorophenyl)propyl]-4-[2-[(2-phenoxyphenyl)-methoxy]ethyl]piperazine dihydrochloride, m.p. 199° C.

1-[3-(3-methoxyphenyl)propyl]-4-[2-[(2-phenoxyphenyl)-methoxy]ethyl]piperazine dihydrochloride, m.p. 187° C.

1-[3-(2-methoxyphenyl)propyl]-4-[2-[(2-phenoxyphenyl)methoxy]ethyl]piperazine dihydrochloride, m.p. 186° C.

1-(3-phenylpropyl)-4-[2-[(2-(phenylthio)phenyl)methoxy]ethyl]piperazine dihydrochloride, m.p. 213° C.

1-[3-(2-methoxyphenyl)propyl]-4-[2-[(2-phenylthio)-phenyl)-ethyl]piperazine dihydrochloride, m.p. 186° C.

1-[2-[(3-phenoxyphenyl)methoxy]ethyl]-4-(3-phenylpropyl)-piperazine dihydrochloride, m.p. 216° C.

1-[3-chlorophenyl]-4-[2-[(2-phenoxyphenyl)-methoxy]ethyl]piperazine hydrochloride, m.p. 166° C.

1-[3-(3-chlorophenyl)propyl]-4-[2-[(3-phenoxyphenyl)-methoxy]ethyl]piperazine dihydrochloride, m.p. 212° C.

1-[3-(3-chlorophenyl)propyl]-4-[2-[(4-phenoxyphenyl)-methoxy]ethyl]piperazine dihydrochloride, m.p. 218° C.

1-[3-(2-methoxyphenyl)propyl]-4-[2-[(4-phenoxyphenyl)-methoxy]ethyl]piperazine dihydrochloride, m.p. 201° C.

4-[2-[(2-phenylmethoxyphenyl)methoxy]ethyl-1-(3-phenylpropyl)-piperazine dihydrochloride, m.p. 206° C.

1-[3-(4-methylphenyl)propyl]-4-[2-[(2-phenylmethoxyphenyl]methoxy]ethyl]piperazine dihydrochloride, m.p. 195° C.

1-[3-(2-methoxyphenyl)propyl]-4-[2-[(2-phenylmethoxy)-phenyl]methoxy]ethyl]piperazine dihydrochloride, m.p. 191° C.

1-[2-(2-phenoxyphenyl)methoxy]ethyl]]-4-(3-phenylpropyl)piperazine dihydrochloride, m.p. 216° C.

1-[2-[(5-chloro-2-phenoxyphenyl)methoxy]ethyl]-4-(3-phenylpropyl)piperazine dihydrochloride hemihydrate, m.p. 225° C.

1-[2-[[4-fluoro-2-(4-fluorophenoxy)phenyl]methoxy]ethyl]-4-(3-phenylpropyl)piperazine dihydrochloride, m.p. 216° C.

1-[2-[[4-fluoro-2-(3-fluorophenoxy)phenyl]methoxy]ethyl]-4-(3-phenylpropyl)piperazine dihydrochloride, m.p. 220° C.

1-[3-(2-phenoxyphenyl)propyl]-4-(3-phenylpropyl)piperazine dihydrochloride, m.p. 235° C.

1-(4-(2-phenoxyphenyl)butyl]-4-(3-phenylpropyl)piperazine dihydrochloride, m.p. 242° C.

N-methyl-N-phenyl-2-[[4-(3-phenylpropyl)-1-piperazinyl]2-ethoxyethyl]benzeneamine dihydrochloride, m.p. 221° C.

1-[2-(2-methoxyphenyl)ethyl]-4-[2-(2-phenoxyphenyl)-ethyl]piperazine dihydrochloride, m.p. >240° C.

1-[2-(2-chlorophenyl)ethyl]-4-[2-(2-phenoxyphenyl)-ethyl]piperazine dihydrochloride, m.p. >250° C.

EXAMPLE 5

1-[3-(2-methoxyphenyl)propyl]-4-[2-[3-phenoxyphenyl)-methoxy]ethyl]piperazine dihydrochloride A mixture of 5 g (21.4 mmol) of 1-[3-(2-methoxyphenyl)propyl]piperazine, 6.9 g of (26.2 mmol) 1-(2-chloroethoxy)methyl-3-phenoxybenzene, 3.55 g (25.7 mmol) of powdered anhydrous potassium carbonate and 0.355 g (2.1 mmol) of potassium iodide in 72 ml of methyl isobutyl ketone was refluxed for 48 hours, while stirring. The reaction mixture was evaporated, the residue dissolved in 75 ml of ether and the solution washed with water, dried over MgSO4 and evaporated. The crude product was purified by means of column chromatography over silica with ethyl acetate as the eluent. The fractions collected were dissolved in 30 ml of ethanol, to which 5 ml of 4.9 N HCl in ethanol was added. The clear solution was evaporated in vacuo and the residue crystallized from ethanol/ether. Yield 4.0 g (35%). m.p. 195° C.

EXAMPLE 6

The following compounds were prepared in a manner analogous to that described in Example 5:

1-[3-(3-methoxyphenyl)propyl]-4-[2-[(3-phenoxyphenyl)-methoxy]ethyl]piperazine dihydrochloride, m.p. 208° C.
1-[3-(4-methylphenyl)propyl]-4-[2-[(3-phenoxyphenyl)-methoxy]ethyl]piperazine dihydrochloride, m.p. 221° C.
1-[3-(2-chlorophenyl)propyl]-4-[2-[(3-phenoxyphenyl)-methoxy]ethyl]piperazine dihydrochloride, m.p. 218° C.
1-[2-(2-phenoxyphenyl)ethyl]-4-(3-phenylpropyl)piperazine dihydrochloride, m.p. 248° C.
1-[2-(4-chloro-2-phenoxyphenyl)ethyl]-4-(3phenylpropyl)piperazine dihydrochloride, m.p. 265° C.
1-[2-(5-chloro-2-phenoxyphenyl)ethyl]-4-(3-phenylpropyl)piperazine dihydrochloride, m.p. >270° C.

EXAMPLE 7

(E)-1-[[(2-phenoxyphenyl)methoxy]ethyl]-4-(3-phenyl-2-propenyl)piperazine dihydrochloride 7.82 g (3.58 mmol) of o-phenoxybenzyl chloride dissolved in 8 ml of dimethoxyethane were added dropwise at room temperature to a solution of 8.82 g (35.8 mmol) of (E)-4-(3-phenyl-2-propenyl)-1-piperazineethanol and 4.42 g (39.4 mmol) of potassium tert-butyloxide and 4 g of 3A molecular sieve in 125 ml of dry dimethoxyethane. After stirring for 3 days at 40° C., the mixture was cooled to room temperature. The salts in the solution were filtered off and the solution was evaporated. The residue obtained was purified by means of column chromatography over silica (eluent toluene:ethanol=9:1). The collected fractions were dissolved in ethanol and 5 ml of 4.9 N HCl in ethanol was added. The clear solution was evaporated. Yield 2.4 g (13%), m.p. 221° C.

EXAMPLE 8

The following compounds were prepared in a manner analogous to that described in Example 7:
(Z)-1-[[(2-phenoxyphenyl)methoxy]ethyl]-4-(3-phenyl-2-propenyl)piperazine dihydrochloride, m.p. 199° C.
(Z)-1-[[(3-phenoxyphenyl)methoxy]ethyl]-4-(3-phenyl-2-propenyl)piperazine dihydrochloride, m.p. 197° C.
1-[[(3-phenoxyphenyl)methoxy]ethyl]-4-(3-phenyl-2-propynyl)piperazine dihydrochloride, m.p. 195° C.
1-[[(2-phenoxyphenyl)methoxy]ethyl]-4-(3-phenyl-2-propynyl)piperazine dihydrochloride, m.p. 199° C.

EXAMPLE 9

(Z)-1-[[(3-phenoxyphenyl)methoxy]ethyl]-4-(3-phenyl-2-propenyl)piperazine dihydrochloride 2.10 g (5 mmol) of 1-[[(3-phenoxyphenyl)methoxy]ethyl]-4-(3-phenyl-2-propynyl)piperazine were dissolved in 40 ml of toluene. 0.32 g of Lindlar catalyst was then added. After shaking under hydrogen in a PARR apparatus ($P_o$=25 psi) for one and a half hours the catalyst was filtered off over Hyflo.

The toluene was evaporated off and the oil obtained was then chromatographed over silica (eluent toluene:ethanol 9:1). The collected fractions were dissolved in ethanol and 2.1 eq. HCl in ethanol was added. The clear solution was evaporated. Yield: 1.67 g (67%). m.p. 197° C.

EXAMPLE 10

1-[[(3-phenoxyphenyl)methoxy]ethyl]piperazine dihydrochloride 1.5 g (4.4 mmol) of 1-formyl-4-[2-[(3-phenoxyphenyl)-methoxy]ethyl]piperazine suspended in 15 ml of 4 N NaOH were refluxed for 26 hours while stirring vigorously, cooled to room temperature, diluted with 15 L of water and extracted with 3×30 ml of ether. The combined ether layers were dried over MgSO4 and evaporated. The solid substance was dissolved in 10 ml of dry ether and 2 ml of 4.9 N HCl in ethanol was added. The precipitate was filtered off and recrystallized from ethanol/ether. Yield 1.3 g (76%) m.p. 171° C.

What is claimed:

1. Aromatic compounds of the formula I comprising:

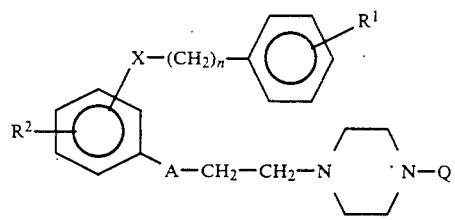

wherein
$R^1$ is a compound selected from the group consisting of hydrogen, $NO_2$, OH, halogen, $C_1$-$C_4$ alkyl, $C_1$-$C_4$ alkoxy, unsubstituted amino and $C_1$-$C_4$ alkyl substituted amino;
$R^2$ is a compound selected from the group consisting of hydrogen, $NO_2$, OH, halogen, $C_1$-$C_4$ alkyl, $C_1$-$C_4$ alkoxy, unsubstituted amino and $C_1$-$C_4$ alkyl substituted amino;
X is a compound selected from the group consisting of O, S, $CH_2$, NH and NALK;
A is a compound selected from the group consisting of $C_mH_{2m}$ and $C_kH_{2k}O$;
k is 1 to 4;
m is 0 to 2;
n is 0 or 1;
Q is a compound selected from the group consisting of hydrogen, phenyl, substituted phenyl and an ALK group optionally substituted by phenyl or substituted phenyl, where the substituted phenyl is phenyl substituted by OH, halogen, $NO_2$, unsubstituted amino, $C_1$-$C_4$ alkyl substituted amino, $C_1$-$C_4$ alkyl or $C_1$-$C_4$ alkoxy, wherein ALK is a $C_1$-$C_4$ aliphatic hydrocarbon;

and when $R^1$ is H, $R^2$ is methoxy, O is phenyl, A is $C_mH_{2m}$, m=0 and n=1, X is selected from the group consisting of S, $CH_2$, NH or NALK; or the acid addition salts thereof.

2. Compounds according to claim 1, of the formula II comprising:

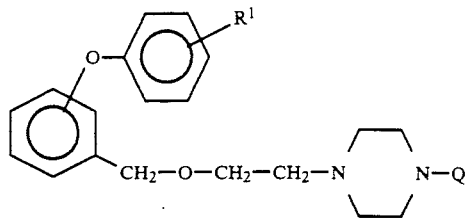

3. Compounds according to claim 2, of the formula III comprising:

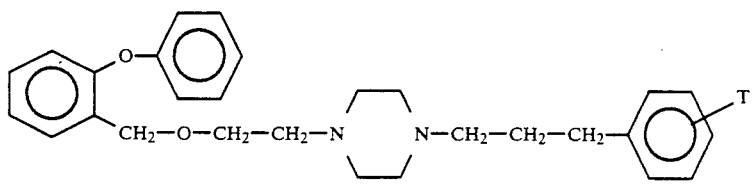

wherein T is a compound selected from the group consisting of hydrogen $C_1$-$C_4$ alkyl and an amino group.

4. Compounds according to claim 2, of the formula IV comprising:

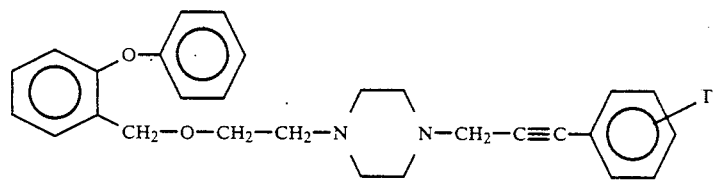

wherein T is a compound selected from the group consisting of hydrogen, $C_1$-$C_4$ alkyl and an amino group.

5. A pharmaceutical preparation comprising a pharmaceutically effective amount for the inhibition of monoamine uptake of at least one compound according to claim 1, in an admixture with a pharmaceutically acceptable carrier or diluent.

* * * * *